United States Patent
Mastrototaro et al.

[11] Patent Number: 5,951,521
[45] Date of Patent: *Sep. 14, 1999

[54] SUBCUTANEOUS IMPLANTABLE SENSOR SET HAVING THE CAPABILITY TO REMOVE DELIVER FLUIDS TO AN INSERTION SITE

[75] Inventors: John J. Mastrototaro, Los Angeles; Clifford W. Hague, Sherman Oaks, both of Calif.

[73] Assignee: MiniMed Inc., Sylmar, Calif.

[ * ] Notice: This patent is subject to a terminal disclaimer.

[21] Appl. No.: 09/161,128

[22] Filed: Sep. 25, 1998

[51] Int. Cl.$^6$ ........................................ A61M 5/32
[52] U.S. Cl. .................. 604/174; 604/44; 604/48; 604/93; 604/180; 606/347
[58] Field of Search .................. 604/27, 43, 44, 604/48, 93, 244, 256, 264, 272, 280, 284, 541, 174, 180; 600/345, 347, 372, 373, 377

[56] References Cited

U.S. PATENT DOCUMENTS

| | | |
|---|---|---|
| 4,562,751 | 1/1986 | Nason et al. . |
| 4,573,994 | 3/1986 | Fischell et al. . |
| 4,678,408 | 7/1987 | Nason et al. . |
| 4,685,903 | 8/1987 | Cable et al. . |
| 5,299,571 | 4/1994 | Mastrototaro . |
| 5,390,671 | 2/1995 | Lord et al. . |
| 5,391,250 | 2/1995 | Cheney, II et al. . |
| 5,482,473 | 1/1996 | Lord et al. . |
| 5,586,553 | 12/1996 | Halili et al. . |

*Primary Examiner*—Ronald Stright
*Assistant Examiner*—Jeremy Thissell
*Attorney, Agent, or Firm*—MiniMed Inc.

[57] ABSTRACT

An implantable subcutaneous set for mounting onto a skin of a user and contacting a subcutaneous placement site beneath the skin includes a base, a cannula, an insertion device and an externally extending conduit. The base is used to secure the implantable subcutaneous set to the skin of the user. The cannula is coupled to and extends from the base. Also, the cannula has at least one lumen with an end for fluid communication with the subcutaneous placement site. In addition, the cannula has at least one port formed near another end of the lumen opposite the end for fluid communication. The insertion device is operatively coupled to the implantable subcutaneous set and the cannula to facilitate insertion of the cannula to contact the subcutaneous placement site. Also, the insertion device may be withdrawn from the subcutaneous set and the cannula after placing the cannula in contact with the subcutaneous placement site. The externally extending conduit is in fluid communication with the at least one port of the cannula to facilitate removal of a fluid that builds up around the at least one lumen of the cannula after insertion of the cannula to substantially prevent degradation of performance of the implantable subcutaneous set while in contact with the subcutaneous placement site. The build up of the fluids are bodily fluids of the user that pool around the port in the at least one lumen of the cannula, and the pool of fluids degrades the performance of the implantable subcutaneous set by obscuring access of other bodily fluids to the at least one lumen of the cannula.

15 Claims, 3 Drawing Sheets

SUBCUTANEOUS IMPLANTABLE SENSOR SET HAVING THE CAPABILITY TO REMOVE DELIVER FLUIDS TO AN INSERTION SITE

FIELD OF THE INVENTION

This invention relates to improved subcutaneous sensor placement and infusion devices and, in particular embodiments, to devices and methods for placing an implantable subcutaneous sensor set at a selected insertion site within the body of a user, which has the capability to remove fluid buildups and/or deliver selected fluids to the selected insertion site.

BACKGROUND OF THE INVENTION

Over the years, a variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings can be especially useful in monitoring and/or adjusting a treatment regimen which typically includes the regular administration of insulin to the patient. Thus, blood glucose readings are particularly useful in improving medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference.

Generally, small and flexible electrochemical sensors can be used to obtain periodic readings over an extended period of time. In one form, flexible subcutaneous sensors are constructed in accordance with thin film mask techniques in which an elongated sensor includes thin film conductive elements encased between flexible insulative layers of polyimide sheets or similar material. Such thin film sensors typically include a plurality of exposed electrodes at one end for subcutaneous placement with a user's blood, or the like, and a corresponding exposed plurality of conductive contacts at another end for convenient external electrical connection with a suitable monitoring device. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571.

Drawbacks to conventional implantable sensors arise from the initial subcutaneous insertion and from the extended presence of the sensor at the subcutaneous insertion site. For example, the area surrounding the implantable sensor may swell or fill with fluid that impedes the ability of the implantable sensor to provide accurate results. This represents a potential health hazard, since less accurate information could lead to erroneous dosing of medication or the like. Another drawback that results from a sensor being inserted for extended periods of time is that it is more prone to infection, which is a health hazard and can also result in fluid buildup and inaccurate readings. To overcome these drawbacks of inaccurate readings and the possibility of infection, the implantable sensor is removed from the subcutaneous site and a new implantable sensor is inserted at a different subcutaneous insertion site. While this solution does provide more accurate readings or reduces the occurrence of infections, it is expensive due to the increased number of implantable sensors needed, and is painful for the user who must insert implantable sensors in more locations and on a more frequent basis.

SUMMARY OF THE DISCLOSURE

It is an object of an embodiment of the present invention to provide an improved implantable sensor set, which obviates for practical purposes, the above mentioned limitations.

According to an embodiment of the invention, an implantable subcutaneous set for mounting onto the skin of a user and contacting a subcutaneous placement site beneath the skin includes a base, a cannula, an insertion device and an externally extending conduit. The base is used to secure the implantable subcutaneous set to the skin of the user. The cannula is coupled to and extends from the base. Also, the cannula has at least one lumen with an end for fluid communication with the subcutaneous placement site. In addition, the cannula has at least one port formed near another end of the lumen opposite the end for fluid communication. The insertion device is operatively coupled to the implantable subcutaneous set and the cannula to facilitate insertion of the cannula to contact the subcutaneous placement site. Also, in some embodiments, the insertion device is withdrawn from the subcutaneous set and the cannula after placing the cannula in contact with the subcutaneous placement site. The externally extending conduit is in fluid communication with the at least one port of the cannula to facilitate removal of fluid that builds up around the at least one lumen of the cannula after insertion of the cannula. Removal of the fluid will substantially prevent degradation of performance of the implantable subcutaneous set while in contact with the subcutaneous placement site. The build up of the fluids are bodily fluids of the user that pool around the port in the at least one lumen of the cannula, and the pool of fluids degrades the performance of the implantable subcutaneous set by obscuring access of other bodily fluids to the at least one lumen of the cannula.

In preferred embodiments, the externally extending conduit includes a septum covering one end of the externally extending conduit to inhibit exposure to external contaminates and facilitate removal of built up fluid by a syringe. Also, the externally extending conduit may include a lumen that extends from the base and an external port and guide for the syringe. In some embodiments, the externally extending conduit is capable of introducing fluids into the subcutaneous placement site by a medication delivery device. Further embodiments include a flexible sensor having a connection portion that is coupled to the base, and a sensor portion that is exposed by the port in the at least one lumen of the cannula to determine characteristics of the user at the subcutaneous placement site.

In particular embodiments, the externally extending conduit includes a filter covering one end of the externally extending conduit to inhibit exposure to external contaminates, and also includes wicking materials to facilitate removal of built up fluid by a wicking process. The externally extending conduit may also include a lumen that extends from the base and an external port and guide for a syringe to remove fluids trapped by the wicking material. Further, the externally extending conduit may be capable of introducing fluids into the subcutaneous placement site by a medication delivery device.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
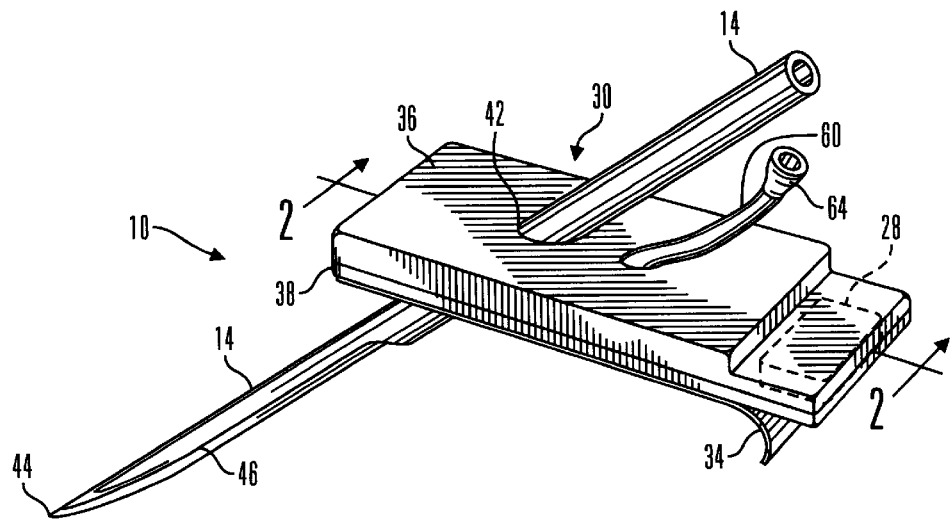
FIG. 1 is a is a perspective view illustrating a subcutaneous sensor insertion set embodying the novel features of the invention.

As shown in the drawings for purposes of illustration, the invention is embodied in a subcutaneous implantable sensor set that includes an implantable sensor that is coupled to a monitor for determining body characteristics. In preferred embodiments of the present invention, the implantable sensor set and monitor are for determining glucose levels in the blood and/or bodily fluids of the user, and the implantable sensor set is capable of reducing the build up of fluid surrounding the implanted implantable sensor. However, it will be recognized that further embodiments of the invention may be used to determine the levels of other agents, characteristics or compositions. In other embodiments, the implantable sensor set may also include the capability to introduce fluids or compositions into the area surrounding the implantable sensor set and implantable sensor. The implantable sensor set and implantable sensor are primarily adapted for use in subcutaneous human tissue. However, still further embodiments may be placed in other types tissue, such as muscle, lymph, organ tissue or the like, and used in animal tissue.

As shown in FIG. 1, an improved implantable subcutaneous sensor set 10 is provided for subcutaneous placement of a flexible sensor 12 (see FIG. 2), or the like, at a selected site in the body of a user. The implantable sensor set 10 includes a hollow, slotted insertion needle 14, and a cannula 16. The needle 14 is used to facilitate quick and easy subcutaneous placement of the cannula 16 at the subcutaneous insertion site. The cannula 16 includes a sensor portion 18 of the sensor 12 to expose one or more sensor electrodes 20 to the user's bodily fluids through a window 22 formed in the cannula 16. After insertion, the insertion needle 14 is withdrawn to leave the cannula 16 with the sensor portion 18 and the sensor electrodes 20 in place at the selected insertion site.

In preferred embodiments, the implantable subcutaneous sensor set 10 facilitates accurate placement of a flexible thin film electrochemical sensor 12 of the type used for monitoring specific blood parameters representative of a user's condition. The subcutaneous sensor set 10 is designed to place the sensor 12 subcutaneously, or at another selected site within the body of a user, in a manner minimizing patient discomfort and trauma. In preferred embodiments, the sensor 12 monitors blood glucose levels, and may be used in conjunction with automated or semi-automated medication infusion pumps of the external or implantable type as described in U.S. Pat. Nos. 4,562,751; 4,678,408; 4,685,903 or 4,573,994, to deliver insulin to a diabetic patient.

Preferred embodiments of the flexible electrochemical sensor 12 are constructed in accordance with thin film mask techniques to include elongated thin film conductors embedded or encased between layers of a selected insulative material such as polyimide film or sheet. The sensor electrodes 20 at a tip end of the sensor portion 18 are exposed through one of the insulative layers for direct contact with patient blood, or other bodily fluids, when the sensor 12 is subcutaneously placed at an insertion site. The sensor portion 18 is joined to a connection portion 24 (see FIG. 2) that terminates in conductive contact pads, or the like, which are also exposed through one of the insulative layers. As is known in the art, and illustrated schematically in FIG. 2, the connection portion 24 and the contact pads are adapted for electrical connection to a suitable monitor 26 for monitoring a user's condition in response to signals derived from the sensor electrodes 20. Further description of flexible thin film sensors of this general type is found in U.S. Pat. No. 5,391,250, entitled METHOD OF FABRICATING THIN FILM SENSORS, which is herein incorporated by reference. The connection portion 24 may be conveniently connected electrically to the monitor 26 by a connector block 28 (or the like) as shown and described in U.S. Pat. No. 5,482,473, entitled FLEX CIRCUIT CONNECTOR, which is also herein incorporated by reference.

Figure 2:
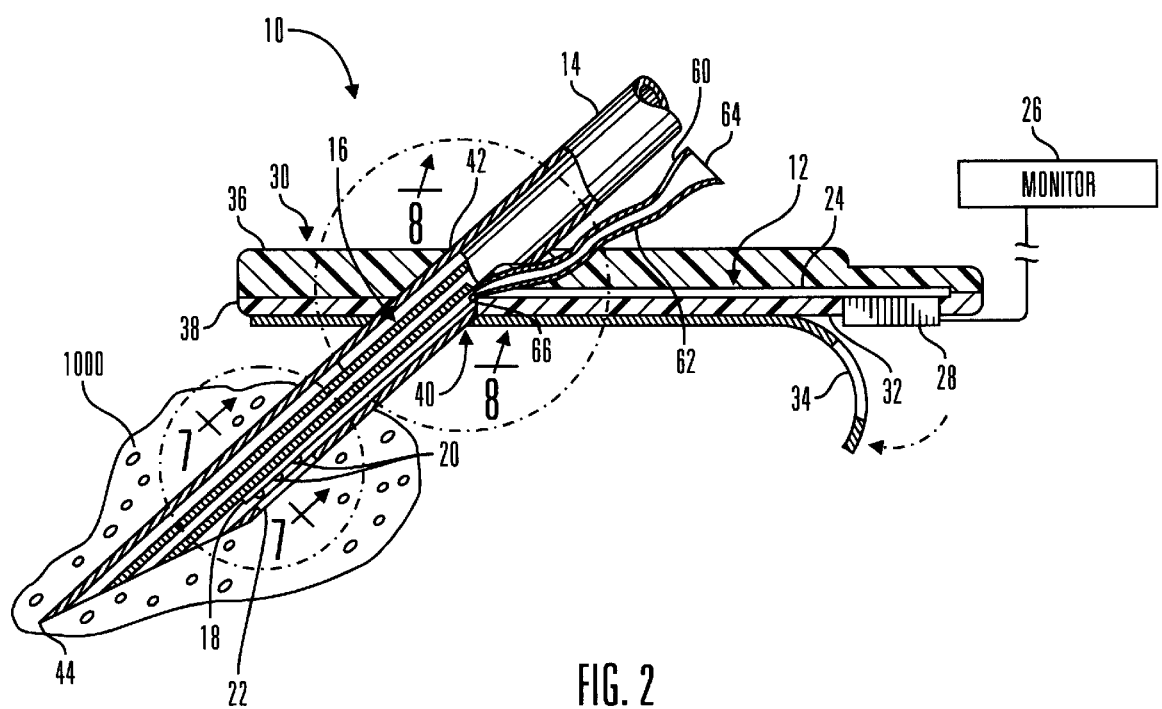
FIG. 2 is an enlarged longitudinal vertical section taken generally on the line 2—2 of FIG. 1.
Figure 3:
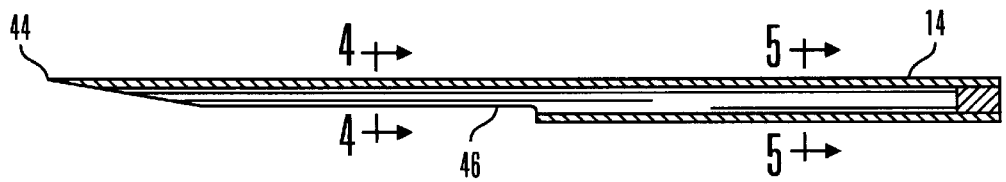
FIG. 3 is an enlarged longitudinal sectional of a slotted insertion needle used in the insertion set of FIGS. 1 and 2.
Figure 4:
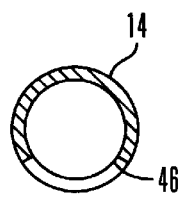
FIG. 4 is an enlarged transverse section taken generally on the line 4—4 of FIG. 3.
Figure 5:
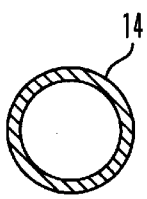
FIG. 5 is an enlarged transverse section taken generally on the line 5—5 of FIG. 3.

The sensor 12 is mounted in a mounting base 30 adapted for placement onto the skin of a user. As shown, the mounting base 30 is a generally rectangular pad having an underside surface coated with a suitable pressure sensitive adhesive layer 32, with a peel-off paper strip 34 normally provided to cover and protect the adhesive layer 32, until the sensor set 10 is ready for use. As shown in FIGS. 1 and 2, the mounting base 30 includes upper and lower layers 36 and 38, with the connection portion 24 of the flexible sensor 12 being sandwiched between the layers 36 and 38. The connection portion 24 has a forward section joined to the sensor portion 18 of the sensor 12, which is folded angularly to extend downwardly through a bore 40 formed in the lower base layer 38. In preferred embodiments, the adhesive layer 32 includes an anti-bacterial agent to reduce the chance of infection; however, alternative embodiments may omit the agent. In further alternative embodiments, the mounting base may be other shapes, such as circular, oval, hour-glass, butterfly or the like.

The insertion needle 14 is adapted for slide-fit reception through a needle port 42 formed in the upper base layer 36 and further through the lower bore 40 in the lower base layer 38. As shown, the insertion needle 14 has a sharpened tip 44 and an open slot 46 which extends longitudinally from the tip 44 at the underside of the needle 14 to a position at least within the bore 40 in the lower base layer 36. Above the mounting base 30, the insertion needle 14 may have a fall round cross-sectional shape, and may be closed off at a rear end of the needle 14. Further description of the needle 14 and the sensor set 10 are found in U.S. Pat. No. 5,586,553, entitled "TRANSCUTANEOUS SENSOR INSERTION SET" and co-pending U.S. patent application Ser. No. 08/871,831, entitled "DISPOSABLE SENSOR INSERTION ASSEMBLY," which are herein incorporated by reference.

Figure 6:
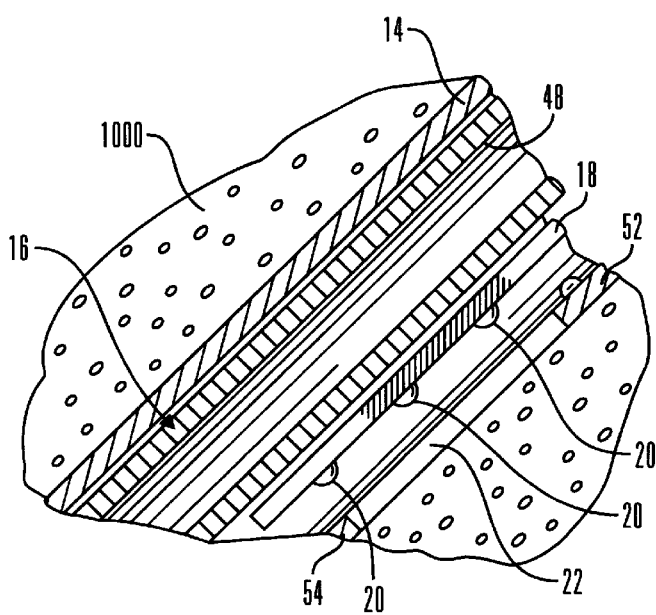
FIG. 6 is an enlarged fragmented sectional view corresponding generally with the encircled region 6 of FIG. 2.
Figure 7:
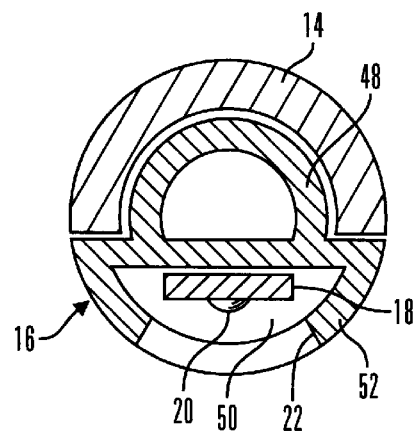
FIG. 7 is an enlarged transverse section taken generally on the line 7—7 of FIG. 2.

The cannula 16 is best illustrated in FIGS. 6 and 7, and includes a first portion 48 having partly-circular cross-section to fit within the insertion needle 14 that extend downwardly from the mounting base 30. In alternative embodiments, the first portion 48 may be formed with a solid core; rather than a hollow core. In preferred embodiments, the cannula 16 is constructed from a suitable medical grade plastic or elastomer, such as polytetrafluoroethylene, silicone, or the like. The cannula 16 also defines an open lumen 50 in a second portion 52 for receiving, protecting and guidably supporting the sensor portion 18 of the sensor 12. The cannula 16 has one end fitted into the bore 40 formed in the lower layer 38 of the mounting base 30, and the cannula 16 is secured to the mounting base 30 by a suitable adhesive, ultrasonic welding, snap fit or other selected attachment method. From the mounting base 30, the cannula 16 extends angularly downwardly with the first portion 48 nested within the insertion needle 14, and terminates slightly before the needle tip 44. At least one window 22 is formed in the lumen 50 near the implanted end 54, in general alignment with the sensor electrodes 20, to permit direct electrode exposure to the user's bodily fluid when the sensor 12 is subcutaneously placed.

In preferred embodiments, shown in FIG. 7, the second portion 52 of the cannula 16 has a partly-circular cross sectional shape which cooperates with the partly-circular shape of the insertion needle 14 to define a substantially full-circle geometry for facilitated insertion through the user's skin. In alternative embodiments, other cross-sections for the needle 14, and first portion 48 and second portion 52 of the cannula 16 may be used, such as rectangular, polygonal, oval or the like. The first portion 48 of the cannula 16 has a generally smaller cross-sectional profile than the second portion 52, for nested sliding reception into the needle 14 to mechanically interlock the needle 14 and cannula 16 to prevent lateral dislocation of the cannula 16 from the insertion needle 14, while permitting longitudinal sliding motion of the needle over the first portion 48 of the cannula 16. The free end of the second portion 52 of the cannula 16 is preferably cut or otherwise set at an oblique angle, as viewed in FIG. 2, to form a continuation of the angle-cut tip 44 of the insertion needle 14.

In use, the implantable sensor set 10 permits quick and easy subcutaneous placement of the sensor portion 18 at a selected site within the body of the user. More specifically, the peel-off strip 34 (see FIG. 1) is removed from the mounting base 30, at which time the mounting base 30 can be pressed onto and seated upon the patient's skin. During this step, the insertion needle 14 pierces the user's skin and carries the protective cannula 16 with the sensor portion 18 to the appropriate subcutaneous placement site. During insertion, the cannula 16 and the needle 14, together, provides a stable support and guide structure to carry the flexible sensor 12 to the desired placement site. When the sensor 12 is subcutaneously placed, with the mounting base 30 seated upon the user's skin, the insertion needle 14 can be slidably withdrawn from the user. During this withdrawal step, the insertion needle 14 slides over the first portion 48 of the protective cannula 16, leaving the sensor portion 18 with electrodes 20 directly exposed to the user's bodily fluids via the window 22. The connection portion 24 is coupled to the monitor 26, so that the sensor 12 can then be used over a prolonged period of time for taking blood chemistry readings, such as blood glucose readings in a diabetic patient. Further description of the needle 14 and the sensor set 10 are found in U.S. Pat. No. 5,586,553, entitled "TRANSCUTANEOUS SENSOR INSERTION SET" and co-pending U.S. patent application Ser. No. 08/871,831, entitled "DISPOSABLE SENSOR INSERTION ASSEMBLY," which are herein incorporated by reference.

In use, implantable subcutaneous sets are generally inserted and used for a period of days or more. Over time it has been found that the performance of the subcutaneous sets degrades in some cases, and that the amount of time that a subcutaneous set can be used varies from individual user to individual user. In subcutaneous sets 10 that include a sensor 12, bodily fluids may begin to form a pool 1000 around the exposed sensor 12 and cannula 16 after insertion and implantation (see FIGS. 2 and 7). This pool 1000 may continue to expand and accumulate over time. Eventually, the presence of the pool 1000 degrades and effects the performance and accuracy of the sensor 12. It is believed that the pool 1000 dilutes the concentrations of various compositions, such as glucose or the like, and may create a "lag" response in the user's other bodily fluids as they enter and mingle with the pool 1000. Thus, the sensor 12 becomes less accurate for detecting small changes in the concentration levels, and tends to report more of a steady state value. In addition, the pool 1000 is relatively stagnant and this increases the possibility of an infection developing. As discussed above, it has been observed that the rate of performance degradation varies from individual to individual, and that when a sensor 12 is removed from the body of an individual user, and tested, the sensor 12 is capable of providing the required accuracy of determining the level of characteristics in a calibration and/or test solution of a known level. Thus, the variation in the amount of time an implantable subcutaneous set 10 can remain in a user's body is dependent on the user and not the sensor 12; and, once fluid is removed from the pool 1000, nominal sensor 12 accuracy is restored and the stagnant fluid is no longer present to provide an opportunity for an infection to develop. Therefore, there is a need to remove the bodily fluid forming the pool 1000 to extend the useful life of an implantable subcutaneous set 10 and to reduce the possibility of developing an infection.

Figure 8:
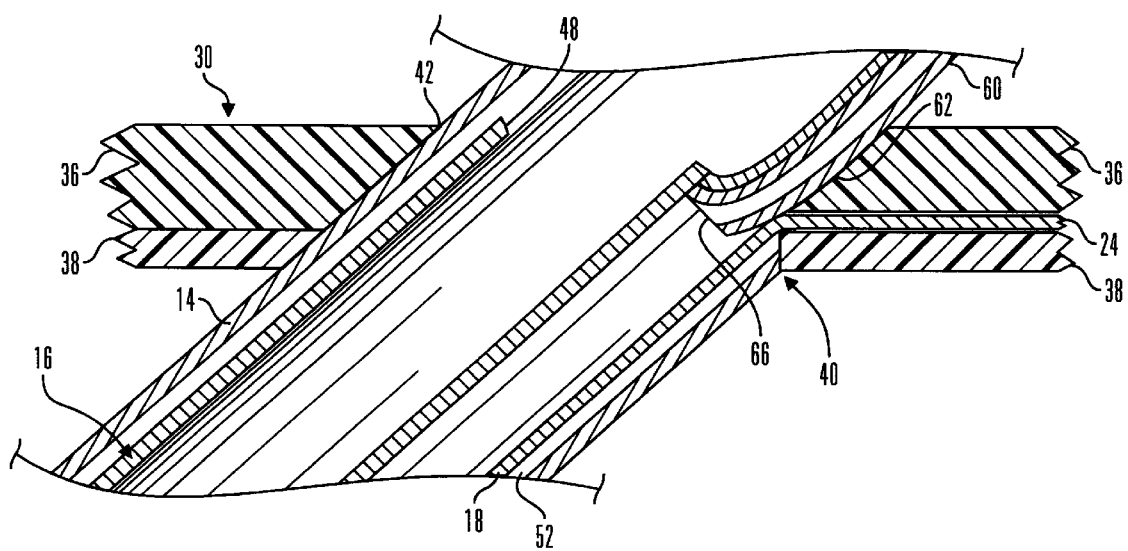
FIG. 8 is an enlarged transverse section taken generally on the line 8—8 of FIG. 2.

As shown in FIGS. 1, 2 and 8, the implantable subcutaneous set 10 includes an additional externally extending lumen 60 in fluid communication with the second portion 52 of the cannula 16. The additional lumen 60 is coupled to the mounting base 30 and communicates with the cannula 16 through a fluid conduit 62 formed in the mounting base 30. In alternative embodiments, the fluid conduit 62 may be formed as an extension of the lumen 60 that is inserted through a bore formed in the mounting base 30 or the like. One end of the lumen 60 is coupled and secured to the mounting base 30 by adhesives, ultrasonic welding, snap fit or other suitable methods. The other end of the lumen 60 includes a syringe port and guide 64 that is used to guide a syringe (not shown) or the like to the lumen 60 to provide fluid communication with the cannula 16. In preferred embodiments, the lumen 60, conduit 62 and the syringe port 64 are formed from a suitable medical-grade plastic material that is bio-compatable. However, in alternative embodiments, the lumen 60, conduit 62 and the syringe port 64 are formed out of other suitable materials, such as metal, glass, composites or the like. In further embodiments, the lumen 60 may be removable from the mounting base 30 when not in use and/or adapted for easy attachment to the mounting base 30 when needed for withdrawing fluids from the body of the user. The lumen 60 may also include an end (not shown) configured to have a snap or friction fit and sufficient structural strength to facilitate attachment to the conduit 62 and the mounting base 30.

In preferred embodiments, the end of the second portion 52 of the cannula 16 includes a septum 66 that provides a seal to substantially inhibit the incursion of external contaminants, such as bacteria, debris, or the like, from entering the cannula 16 and contaminating the subcutaneous placement site. This reduces the likelihood of developing an infection through contact with the external environment. In further embodiments, the lumen 60 and conduit 62 may include an anti-bacterial agent on the interior surface of the lumen 60 or actually formed as an integral part of the lumen 60 and conduit 62 material to further minimize the chance of an all infection.

To remove fluid in the pool 1000 from the area surrounding the cannula 16 and the sensor portion 18 of the sensor 12, the user attaches the lumen 60 and syringe port 64 to the end of the conduit 62 on the mounting base 30 (although in alternative embodiments, the lumen 60 and syringe port 64 may be already in place or formed as part of the set 10). Next, the user introduces a needle of a syringe (not shown), or the like, into the syringe port and guide 64 and pierces the septum 66. The user then generates a vacuum pressure in the syringe, or the like, and this draws out the bodily fluid forming the pool 1000 surrounding the cannula 16 and sensor 12. When sufficient fluid is extracted, the syringe is withdrawn from the syringe port and guide 64. Finally, the lumen 60 and syringe port and guide 64 can be removed. In alternative embodiments, the withdrawn fluid may be used to calibrate and/or control check the sensor 12.

In particular embodiments, to verify that sufficient fluid has been removed, another syringe or medication delivery device may be connected to the lumen 60 and syringe port and guide 64, and a small amount of calibrating fluid of a known is introduced. The sensor 12 output is then analyzed to determine if sufficient fluid was withdrawn and the sensor 12 is still operating within nominal parameters. After the test, the small amount of fluid can be withdrawn, or left at the subcutaneous placement site, if small enough not to effect future readings. The syringe or medication delivery device is then removed, and the user continues to use the implantable subcutaneous set for the full period of extended implantation. After removal of the test solution syringe, the lumen 60 and syringe port and guide 64 can be removed.

In other embodiments, the lumen 60 and conduit 62 may be used to introduce fluids that are capable of cleaning or recharging the sensor 12 for longer period of use. The user would introduce, a non-toxic cleaning agent or recharging fluid, and then withdraw the introduced fluid after a specified period of time.

In alternative embodiments, the lumen 60, the syringe port and guide 64, and septum 66 may be omitted. The conduit 62 is filled with a wicking material (not shown) and the opening of the conduit 62 at the surface of the mounting base 30 is closed off with a filter (not shown) that prevents external contaminants from entering the wicking material and the cannula 16. In preferred embodiments, the filter is porous enough to allow the excess fluid removed by the wicking process to evaporate out of the conduit 62. However, in alternative embodiments, the filter acts as a septum, and a syringe or the like is periodically introduced into the conduit 62 to remove the accumulated fluid. In further alternative embodiments, the wicked away fluid may be used to calibrate and/or control check the sensor 12.

In further embodiments, prior to removal of the subcutaneous set 10, the user may attach a syringe or the like to the lumen 60 or the conduit 62, and introduce an anti-bacterial solution, anti-biotic and/or healing promoting agent to the subcutaneous placement site to facilitate healing and to reduce the risk of infection after removal of the subcutaneous set. In still further embodiments, the excess fluid may be removed from the pool 1000 prior to removal of the subcutaneous set and/or prior to introduction of the anti-bacterial fluid.

In yet another embodiments, a pre-evacuated vacuum tube, or the like, may be used instead of a syringe. In addition, a step motor type pump, continuous pump, automated pump or the like, may be used in place of the syringe for regular withdrawal of the fluid in the pool 1000. In still another embodiment, the fluid is regularly withdrawn using a fluid path that causes the withdrawn fluid to flow over the sensor 12 to assure a regular change of fluid coming in contact with the sensor 12.

In further embodiments of the present invention, the lumen 60 and conduit 62 may be added to an infusion set (not shown) to facilitate removal of fluid that may build up around the outlet of the infusion cannula (not shown) that could impede the infusion or distribution of a medication at a subcutaneous placement site. In addition, the first portion 48 of the cannula 16 can be hollow, as shown in the Figs., to form a second lumen available to deliver medication and/or sensor calibration fluid to the vicinity of the electrodes 20, or alternately to withdraw user bodily fluids. It may also be used in conjunction with the other lumen 52 in the cannula to facilitate multiple flow paths or cooperative flow, such as the introduction and extraction of fluids at the same time.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An implantable subcutaneous set for mounting onto a skin of a user and contacting a subcutaneous placement site beneath the skin, the implantable subcutaneous set comprising:

a base to secure the implantable subcutaneous set to the skin of the user;

a cannula coupled to and extending from the base, wherein the cannula has at least one lumen with an end for fluid communication with the subcutaneous placement site, wherein the cannula also has at least one port formed near another end of the lumen opposite the end for fluid communication;

an insertion device operatively coupled to the implantable subcutaneous set and the cannula to facilitate insertion of the cannula to contact the subcutaneous placement site; and an externally extending conduit in fluid communication with the at least one port of the cannula to facilitate removal of fluid that builds up around the at least one lumen of the cannula after insertion of the cannula to substantially prevent degradation of performance of the implantable subcutaneous set while in contact with the subcutaneous placement site.

2. An implantable subcutaneous set in accordance with claim 1, wherein the externally extending conduit includes a septum covering one end of the externally extending, conduit to inhibit exposure to external contaminates and facilitate removal of built up fluid by a syringe.

3. An implantable subcutaneous set in accordance with claim 2, wherein the externally extending conduit includes a lumen that extends from the base and an external port and guide for the syringe.

4. An implantable subcutaneous set in accordance with claim 2, wherein the externally extending conduit is further useable for introducing fluids into the subcutaneous placement site by a medication delivery device.

5. An implantable subcutaneous set in accordance with claim 2, further including a sensor having a connection portion coupled to the subcutaneous set, and a sensor portion exposed by the at least one port in the at least one lumen of the cannula to determine characteristics of the user at the subcutaneous placement site.

6. An implantable subcutaneous set in accordance with claim 1, wherein the built up fluid is bodily fluids of the user that pool around the at least one port in the at least one lumen of the cannula, and wherein the pool of fluids degrades the performance of the implantable subcutaneous set by obscuring access of other bodily fluids to the at least one lumen of the cannula.

7. An implantable subcutaneous set in accordance with claim 6, further including a flexible sensor having a connection portion coupled to the base, and a sensor portion exposed by the at least one port in the at least one lumen of the cannula to determine characteristics of the user at the subcutaneous placement site.

8. An implantable subcutaneous set in accordance with claim 1, wherein the externally extending conduit includes a filter covering one end of the externally extending conduit to inhibit exposure to external contaminates and a wicking material to facilitate removal of built up fluid by a wicking process.

9. An implantable subcutaneous set in accordance with claim 8, wherein the externally extending conduit includes a lumen that extends from the base and an external port and guide for a syringe to remove fluids trapped by the wicking material.

10. An implantable subcutaneous set in accordance with claim 8, wherein the externally extending conduit is further useable for introducing fluids into the subcutaneous placement site by a medication delivery device.

11. An implantable subcutaneous set in accordance with claim 8, further including a flexible sensor having a connection portion coupled to the base, and a sensor portion exposed by the at least one port in the at least one lumen of the cannula to determine characteristics of the user at the subcutaneous placement site.

12. An implantable subcutaneous set in accordance with claim 1, wherein the insertion device is withdrawable from the subcutaneous set and the cannula after placing the cannula in contact with the subcutaneous placement site.

13. An implantable subcutaneous set in accordance with claim 1, wherein the externally extending conduit is connectable to a pump for removal of built up fluid.

14. An implantable subcutaneous set in accordance with claim 1, further including a sensor having a connection portion coupled to the subcutaneous set, and a sensor portion exposed by the at least one port in the at least one lumen of the cannula to determine characteristics of the user at the subcutaneous placement site, and wherein the externally extending conduit is useable for removal of the built up fluid over the sensor.

15. An implantable subcutaneous set in accordance with claim 1, further including a sensor having a connection portion coupled to the subcutaneous set, and a sensor portion exposed by the at least one port in the at least one lumen of the cannula to determine characteristics of the user at the subcutaneous placement site, and wherein the externally extending conduit is useable for removal of the built up fluid that is useable to calibrate the sensor.

* * * * *